(12) United States Patent
Schermer et al.

(10) Patent No.: US 7,209,836 B1
(45) Date of Patent: Apr. 24, 2007

(54) METHOD AND SYSTEM FOR AUTOMATICALLY CREATING CROSSTALK-CORRECTED DATA OF A MICROARRAY

(75) Inventors: Mack J. Schermer, Belmont, MA (US); Roger D. Dowd, Natick, MA (US); Jun Yang, Santa Monica, CA (US)

(73) Assignee: PerkinElmer LAS, Inc., Waltham, MA (US)

( * ) Notice: Subject to any disclaimer, the term of this patent is extended or adjusted under 35 U.S.C. 154(b) by 0 days.

(21) Appl. No.: 09/354,500

(22) Filed: Jul. 16, 1999

(51) Int. Cl.
 *C12Q 1/68* (2006.01)
 *G06F 19/00* (2006.01)
(52) U.S. Cl. ............... 702/19; 702/20; 435/6
(58) Field of Classification Search ............ 702/19; 364/571.01–582; 382/162–167
 See application file for complete search history.

(56) References Cited

U.S. PATENT DOCUMENTS

| | | | |
|---|---|---|---|
| 5,578,832 A | | 11/1996 | Trulson et al. |
| 5,631,734 A | * | 5/1997 | Stern et al. |
| 5,702,887 A | | 12/1997 | Law et al. |
| 5,728,528 A | | 3/1998 | Mathies et al. |
| 5,733,729 A | * | 3/1998 | Lipshutz et al. |
| 5,795,716 A | * | 8/1998 | Chee et al. |
| 5,804,386 A | | 9/1998 | Ju |
| 5,807,522 A | | 9/1998 | Brown et al. |
| 5,814,454 A | | 9/1998 | Ju |
| 5,821,993 A | | 10/1998 | Robinson |
| 5,853,992 A | | 12/1998 | Glazer et al. |
| 6,040,138 A | * | 3/2000 | Lockhart et al. |
| 6,075,613 A | * | 6/2000 | Schermer et al. |
| 6,225,636 B1 | * | 5/2001 | Ginestet ............ 250/458.1 |
| 6,245,507 B1 | * | 6/2001 | Bogdanov .............. 435/6 |
| 6,251,601 B1 | * | 6/2001 | Bao et al. ............... 435/6 |
| 6,320,196 B1 | * | 11/2001 | Dorsel et al. ........ 250/458.1 |

FOREIGN PATENT DOCUMENTS

| | | |
|---|---|---|
| WO | WO 98/15649 | 4/1998 |
| WO | WO 98/17992 | 4/1998 |

OTHER PUBLICATIONS

Shalon, D. et al., Genome Research, 6(7):639-45, Jul. 1996.*
Schena et al.; Quantitative Monitoring of Gene Expression Patterns with a Complementary DNA Microarray; Science; vol. 270; Oct. 20, 1995; pp. 467-470.

\* cited by examiner

*Primary Examiner*—Marianne P. Allen
(74) *Attorney, Agent, or Firm*—Cesari and McKenna, LLP

(57) ABSTRACT

A method and system are disclosed for automatically creating crosstalk-corrected data of a microarray utilizing calibration dye spots each of which comprises a single pure dye. A microarray scanner, such as a confocal laser microarray scanner, generates dye images, each of which contains at least one of the calibration dye spots for each of the output channels of the scanner. For each of the calibration dye spots, an output of each of the output channels is measured to obtain output measurements. A set of correction factors is computed from the output measurements to correct the data subsequently gathered from the microarray scanner. In other words, the correction factors are applied to quantitation or measurement data obtained from microarray images which contain spots having dyes of known or unknown excitation or emission spectra to obtain crosstalk-corrected data.

16 Claims, 3 Drawing Sheets

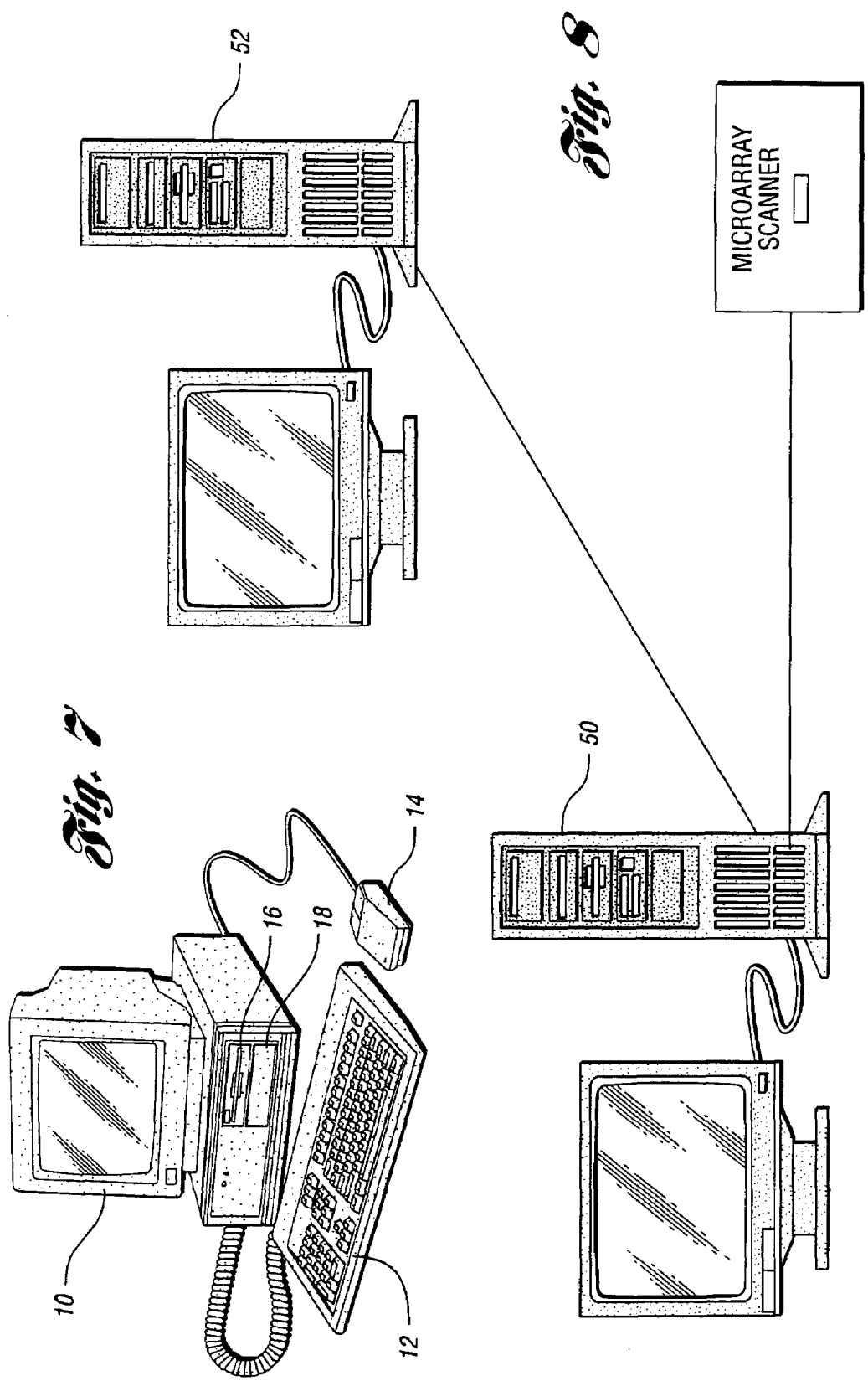

METHOD AND SYSTEM FOR AUTOMATICALLY CREATING CROSSTALK-CORRECTED DATA OF A MICROARRAY

TECHNICAL FIELD

This invention relates to methods and systems for creating crosstalk-corrected data of a microarray and, in particular, to methods and systems for automatically creating crosstalk-corrected data of a microarray utilizing calibration spots.

BACKGROUND ART

Multifluorescence confocal imaging typically utilizes a multi-channel microarray scanner to obtain images of dye spots of a microarray. As illustrated in FIG. 1, microarrays are created with fluorescently labeled DNA samples in a grid pattern consisting of rows 22 and columns 20 typically spread across a 1 by 3 inch glass microscope slide 24. Each spot 26 in the grid pattern 28 represents a separate DNA probe and constitutes a separate experiment. A plurality of such grid pattern comprises an array set 30. Reference or "target" DNA (or RNA) is spotted onto the glass slide 24 and chemically bonded to the surface. Fluorescently labeled "probe" DNA (or RNA) is introduced and allowed to hybridize with the target DNA. Excess probe DNA that does not bind is removed from the surface of the slide 24 in a subsequent washing process.

As illustrated in FIG. 2, a confocal laser microarray scanner or microarray reader is commonly used to scan the microarray slide 24 to produce one image for each dye used by sequentially scanning the microarray with a laser of a proper wavelength for the particular dye. Each dye has a know excitation spectra as illustrated in FIG. 3 and a known emission spectra as illustrated in FIG. 4. The scanner includes a beam splitter 32 which reflects a laser beam 34 towards an objective lens 36 which, in turn, focuses the beam at the surface of slide 24 to cause fluorescent spherical emission. A portion of the emission travels back through the lens 36 and the beam splitter 32. After traveling through the beam splitter 32, the fluorescence beam is reflected by a mirror 38, travels through an emission filter 40, a focusing detector lens 42 and a central pinhole 44. After traveling through the central pinhole 44, the fluorescence beam is detected by a detector, all in a conventional fashion.

The intent of a microarray experiment is to determine the concentrations of each DNA sample at each of the spot locations on the microarray. Further data analysis of the brightness values are typically done to produce a ratio of one dye's brightness to any or all of the other dyes on the microarray. An application of the microarray experiment is in gene expression experiments. Higher brightness values are a function of higher concentrations of DNA. With a microarray, a researcher can determine the amount a gene is expressed under different environmental conditions.

To be accurate, the reader must be able to quantitate the brightness of each microarray spot for each labeled DNA sample used in the experiment. To do this the reader must filter the emissions from any and all other fluorescent samples. The concentration of the DNA is a function of the brightness of the emission when excited by a laser of the proper wavelength. It becomes difficult to differentiate between the emissions of different dyes when the emission spectra of a dye overlaps with another. Furthermore, the brightness produced from the emission of one dye could be contaminated by emissions from another dye. This contamination of the brightness values is commonly known as crosstalk.

Microarray readers have been designed to simultaneously scan more than two dyes using lasers with the proper wavelength. In this type of experiment, multiple samples of DNA are hybridized onto the microarray, each with a different fluorescent label. Crosstalk contamination is equally likely as in the two dye experiments and can even be more troublesome when dyes with close emission spectra are placed on the same microarray.

U.S. Pat. Nos. 5,804,386 and 5,814,454 disclose sets of labeled energy transfer fluorescent primers and their use in multi-component analysis.

U.S. Pat. No. 5,821,993 discloses a method and system for automatically calibrating a color camera in a machine vision system.

The paper by Schena, M., et al., (1995) "Quantitative Monitoring of Gene Expression Patterns With a Complementary DNA Microarray", Science 270; 467–469 is also related to the present invention.

DISCLOSURE OF INVENTION

An object of the present invention is to provide a method and system for creating crosstalk-corrected data of a microarray wherein a sequence of algebraic operations are used to obtain correction factors which, in turn, are used to correct for crosstalk between two or more dyes in a multi-channel imager such as a microarray scanner.

Another object of the present invention is to provide a method and system for creating crosstalk-corrected data of a microarray by utilizing calibration spots on a microarray sample substrate.

In carrying out the above objects and other objects of the present invention, a method is provided for automatically creating crosstalk-corrected data of a microarray. The method includes providing a microarray substrate having calibration dye spots. Each of the calibration dye spots comprises a single pure dye. The method also includes, for each of the calibration dye spots, generating a dye image containing at least one of the calibration dye spots for each of a plurality of output channels and also, for each of the calibration dye spots, measuring an output of each of the output channels to obtain output measurements. The method further includes computing a set of correction factors from the output measurements and applying the set of correction factors to data obtained from microarray images containing spots having dyes with excitation or emission spectra to obtain crosstalk-corrected data.

Preferably, the step of generating includes the step of imaging the calibration dye spots to produce a dye image for each calibration dye spot.

Preferably, the substrate is a glass slide.

Also, preferably, each of the channels is optimized for a different dye and the step of generating is performed by an imager such as a microarray scanner or a camera.

Preferably, each of the dyes is a fluorescent dye.

Preferably, the step of computing includes the step of computing crosstalk ratios based on spot brightness values for each of the calibration dye spots on each of the output channels.

Preferably, the number of calibration dye spots is more than or equal to the number of dyes.

The calibration dye spots may be hybridized target DNA and fluorescently labeled probe DNA.

Still further in carrying out the above objects and other objects of the present invention, a system is provided for carrying out the above method steps.

In the method and system of the present invention, crosstalk correction requires the availability and use of calibration spots on the microarray. As illustrated in FIG. 5, these calibration spots should be composed of the highest concentration of each single probe or dye that could be obtained by the microarray process being utilized. By measuring the crosstalk between the calibration spots, one can obtain all of the information that is needed to correct for crosstalk in all spots of the microarray without explicit knowledge of the dyes' excitation or emission characteristics.

In the case of 'n' samples on the microarray experiment with each DNA sample labeled (i.e., typically 1000–5000 spots but only 2–4 dyes), the number of crosstalk calibration spots is typically greater than or equal to the number of dyes used. More calibration spots can be used to better tolerate experimental abnormalities. In the case of additional calibration spots, all the spots of an identical dye can be averaged together. The dyes used to create the calibration spots should also be the same as were used to label the DNA samples as illustrated in FIG. 6.

The above objects and other objects, features and advantages of the present invention are readily apparent from the following detailed description of the best mode for carrying out the invention when taken in connection with the accompanying drawings.

BRIEF DESCRIPTION OF DRAWINGS

FIG. 7 is a schematic diagram illustrating a preferred hardware configuration on which the computational portion of the method of the present invention can be implemented; and FIG. 8 is a schematic view of a system in which the present invention can be utilized.

BEST MODE FOR CARRYING OUT THE INVENTION

Figure 1:
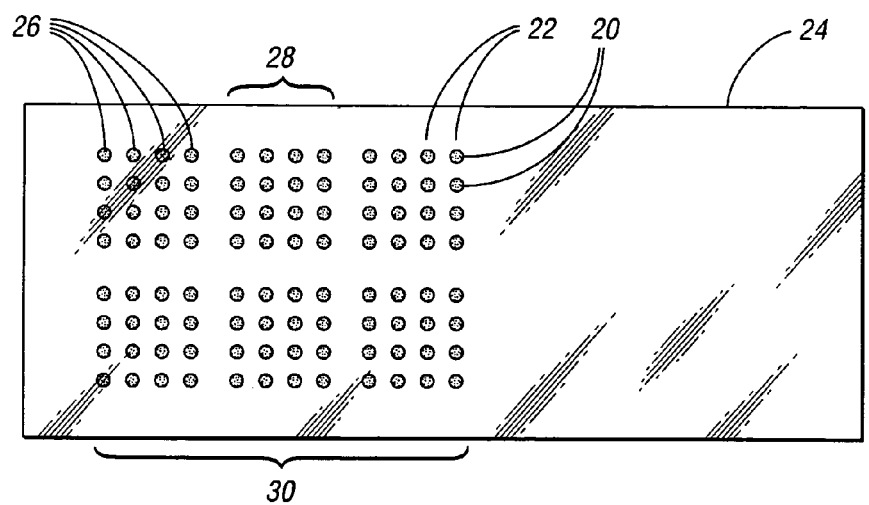
FIG. 1 is a top plan schematic view illustrating a spot, an array and an array set on a glass slide.

Referring now to the drawing figures, there is illustrated in FIG. 7 a workstation on which the computational portion of the method and system of the present invention can be implemented. However, other configurations are possible. The hardware illustrated in FIG. 7 includes a monitor 10 such as a single SVGA display, a keyboard 12, a pointing device such as a mouse 14, a magnetic storage device 16, and a chassis 18 including a CPU and random access memory. The monitor 10 may be a touch screen monitor used in addition to standard keyboard/mouse interaction. In a preferred embodiment, the chassis 18 is a Pentium-based IBM compatible PC or other PC having at least 32 megabytes of RAM and at least 12 megabytes of hard disk space.

The workstation typically includes a Windows NT, graphical user interface as well as an Ethernet 10 Base-T high speed Lan network interface.

Figure 2:
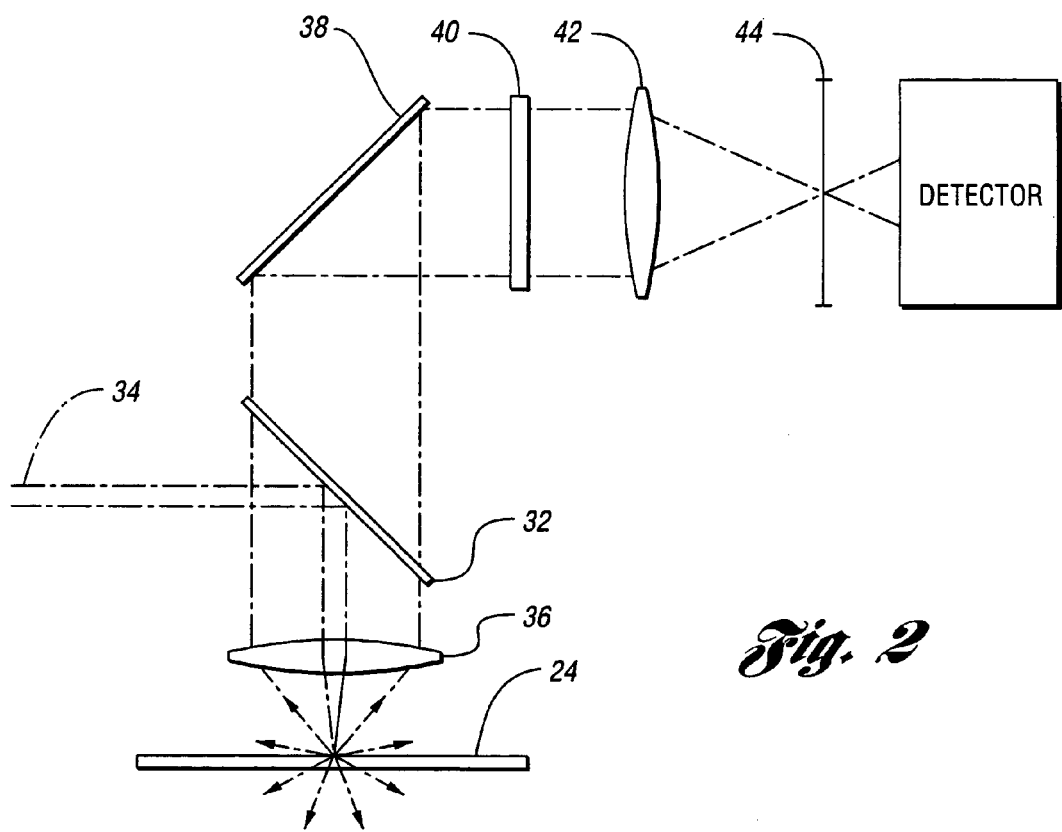
FIG. 2 is a schematic view of a confocal laser reader used to generate digital images.
Figure 3:
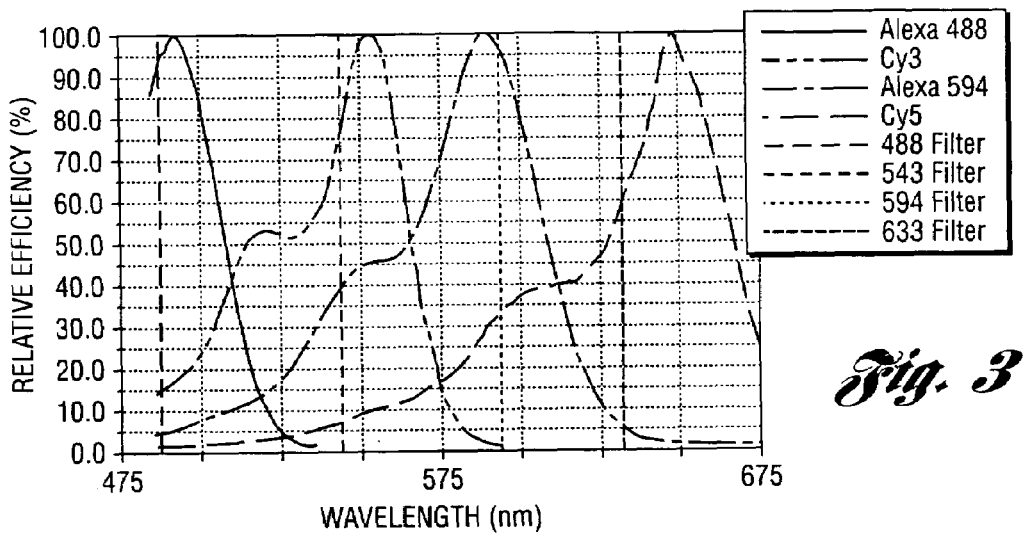
FIG. 3 illustrates graphs of sample excitation spectra.
Figure 4:
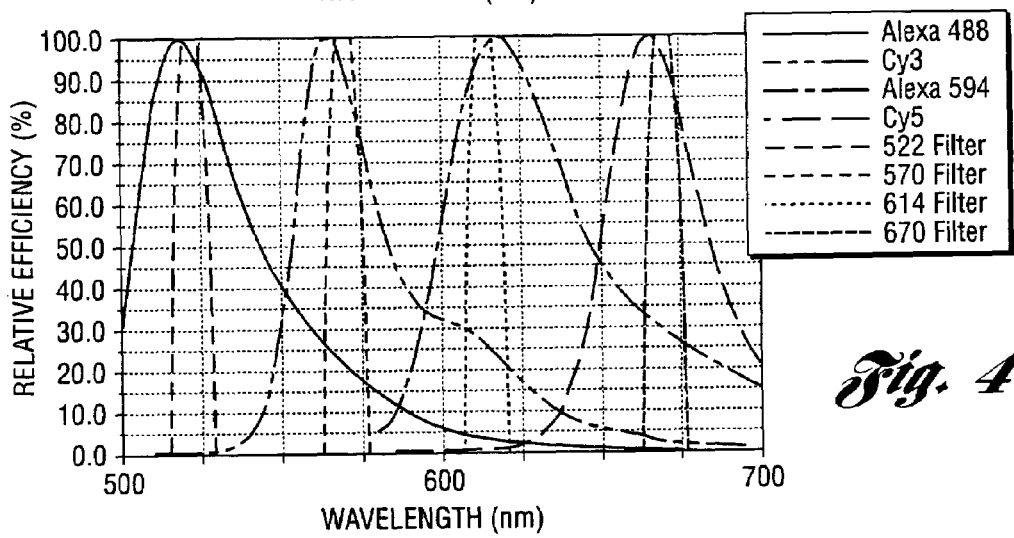
FIG. 4 illustrates graphs of sample emission spectra.

One or more images are obtained by a user from the microarray reader or scanner of FIGS. 2 and 8. The scanner is controlled by a scanner control computer 50 which, in turn, is also networked to a quantitation computer 52.

Calibration in the Two Channel Microarray Experiment

Figure 5:
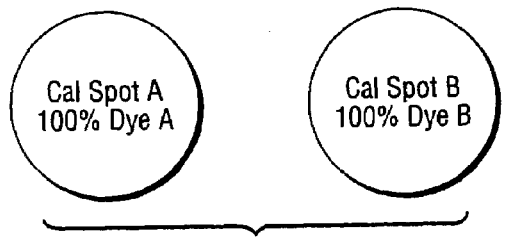
FIG. 5 is a schematic view of calibration spots with two dyes.
Figure 6:
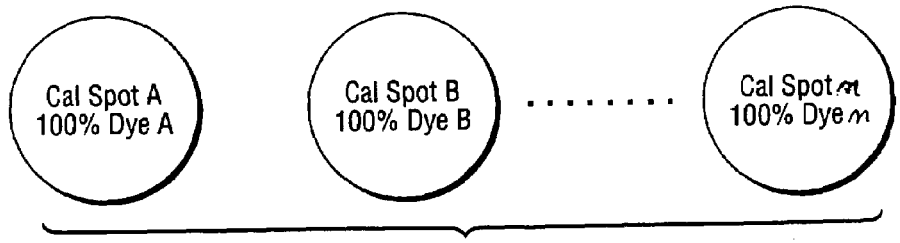
FIG. 6 is a schematic view of calibration spots with 'n' dyes.

Assume that the user has provided two microarray spots for calibration as illustrated in FIG. 5. Further assume two-color, two-channel scanning, with the microarray reader's channels balanced on these two calibration spots. The two dyes are called "Dye A" and "Dye B," and the instrument channels are called "Channel 1" and "Channel 2." Channel 1 is optimized for Dye A, and Channel 2 is optimized for Dye B. These calibration spots should contain "pure" dye, or more precisely, the maximum labeled-DNA concentration associated with 100% gene expression.

These calibration spots are referred to as Cal Spot A and Cal Spot B. Before scanning them, the channels of the reader are balanced to produce roughly equivalent brightness values on a spot other than a Cal Spot. Crosstalk is a relatively small (2–5%) signal in the opposite channel. The two dots are scanned, both dots on both channels, and the scan data analyzed to produce spot brightness values. The four resulting data values are named as follows:

CalBrightA1=spot brightness value of Cal Spot A scanned on Channel 1

CalBrightA2=spot brightness value of Cal Spot A scanned on Channel 2

CalBrightB1=spot brightness value of Cal Spot B scanned on Channel 1

CalBrightB2=spot brightness value of Cal Spot B scanned on Channel 2

Crosstalk ratios are defined as follows:

$$CrosstalkA = CalBrightA2/CalBrightA1$$

$$CrosstalkB = CalBrightB1/CalBrightB2$$

These two measured Crosstalk values (which are each a fraction less than 1) are stored for use in correcting values on all of the other dots on the array.

Correction in the Two Channel Microarray Experiment

The other dots in the array have random combinations of Dye A and Dye B in unknown ratios. Each dot is scanned on both Channel 1 and Channel 2, and those two raw brightness values are corrected for crosstalk. The first-order method for doing that is as follows.

Define more terms: "Brightness" is the measured intensity value for a spot from a particular instrument channel. "Signal" (1 and 2) is the portion of brightness (presumably the large majority) which is from the target dye (e.g., not crosstalk). "Signal" (1 and 2) is the answer that is sought.

| Unknowns: | Signal 1 = $S_1$ |
| --- | --- |
| | Signal 2 = $S_2$ |
| Knowns: | What is measured on each spot |
| | Brightness 1 = $B_1$ |
| | Brightness 2 = $B_2$ |
| | From the two channel calibration section |
| | Crosstalk$_{12}$ = $\alpha_{12}$ |
| | Crosstalk$_{21}$ = $\alpha_{21}$ |

Signal n for each spot on the array can then be determined by the following equations:

$$B_1 = S_1 + S_2\alpha_{12}$$

$$B_2 = S_2 + S_1\alpha_{21}$$

or, solving for Signal:

$$S_1 = (B_1 - (\alpha_{12} \times B_2))/(1 - (\alpha_{12} \times \alpha_{21}))$$

$$S_2 = (B_2 - (\alpha_{21} \times B_1))/(1 - (\alpha_{12} \times \alpha_{21}))$$

Calibration and Correction in the 'n' Channel Microarray Experiment

Scanners with 3, 4, or more channels are perhaps even more likely to suffer from crosstalk than 2-channel instruments. Correction for this is accomplished using the same calibration spot technique, and the measurement of the crosstalk contribution of all of the combinations of excitation wavelengths and dyes.

To generalize some definitions of terms:

| | |
|---|---|
| $\alpha_{xy}$ = | measured and calculated crosstalk ratio of Dye Y into the Dye X channel |
| $S_x$ = | Signal from Dye X (which one is seeking) |
| $B_x$ = | Measured brightness of an arbitrary spot on the Dye X channel |

Then, for the 3-channel case, the equations are as follows:

$$B_1 = S_1 + S_2\alpha_{12} + S_3\alpha_{13}$$

$$B_2 = S_1\alpha_{21} + S_2 + S_3\alpha_{23}$$

$$B_3 = S_1\alpha_{31} + S_2\alpha_{32} + S_3$$

which, in matrix form looks like:

$$[B_x] = [S_x][A] \text{ where } A = \begin{bmatrix} 1 & \alpha_{12} & \alpha_{13} \\ \alpha_{21} & 1 & \alpha_{23} \\ \alpha_{31} & \alpha_{32} & 1 \end{bmatrix}$$

$$DET A = 1 - \alpha_{12}\alpha_{21} - \alpha_{13}\alpha_{31} - \alpha_{23}\alpha_{32} + \alpha_{13}\alpha_{21}\alpha_{32} + \alpha_{12}\alpha_{23}\alpha_{31}$$

$$S_1 = \frac{B_1(1 - \alpha_{23}\alpha_{32}) - B_2(\alpha_{12} - \alpha_{13}\alpha_{32}) + B_3(\alpha_{12}\alpha_{23} - \alpha_{13})}{DET A}$$

$$S_2 = \frac{-B_1(\alpha_{21} - \alpha_{31}\alpha_{23}) + B_2(1 - \alpha_{31}\alpha_{13}) - B_3(\alpha_{23} - \alpha_{21}\alpha_{13})}{DET A}$$

$$S_3 = \frac{B_1(\alpha_{21}\alpha_{32} - \alpha_{31}) - B_2(\alpha_{32} - \alpha_{12}\alpha_{31}) + B_3(1 - \alpha_{12}\alpha_{21})}{DET A}$$

The expansion of this matrix from 3×3 to 4×4 (or n×n) is straightforward.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for automatically creating crosstalk-corrected data of a microarray wherein crosstalk is caused by overlapping dye emission spectra, the method comprising:

providing a microarray substrate having three or more calibration dye spots, each of the calibration dye spots comprising a single pure dye;

for each of the calibration dye spots, generating a dye image containing at least one of the calibration dye spots for each of a plurality of output channels;

for each of the calibration dye spots, measuring an output of each of the output channels to obtain output measurements;

computing a set of correction factors from the output measurements by computing crosstalk ratios based on spot brightness values for each of the calibration dye spots on each of the output channels wherein the spot brightness value includes the crosstalk contribution of all of the combinations of excitation wavelengths and dyes;

applying the set of correction factors to quantitation data obtained from the generated microarray images containing spots having three or more dyes with excitation or emission spectra to obtain crosstalk-corrected data; and displaying or storing in memory said crosstalk-corrected data.

2. The method as claimed in claim 1 wherein the step of generating includes the step of imaging the calibration dye spots to produce a dye image for each calibration dye spot.

3. The method as claimed in claim 1 wherein the substrate is a glass slide.

4. The method as claimed in claim 1 wherein each of the channels is optimized for a different dye.

5. The method as claimed in claim 1 wherein the step of generating is performed by an imager.

6. The method as claimed in claim 1 wherein each of the dyes is a fluorescent dye.

7. The method as claimed in claim 1 wherein the number of calibration dye spots is more than or equal to the number of dyes.

8. The method as claimed in claim 1 wherein the calibration dye spots are hybridized target DNA and fluorescently labeled probe DNA.

9. A system for automatically creating crosstalk-corrected data of a microarray wherein crosstalk is caused by overlapping dye emission spectra, the system comprising:

a microarray substrate having three or more calibration dye spots, each of the calibration dye spots comprising a single pure dye;

an imager having a plurality of output channels wherein for each of the calibration dye spots the imager generates a dye image containing at least one of the calibration dye spots for each of the output channels; and a computer programmed to (a) obtain output measurements from each of the output channels for each of the calibration dye spots;

(b) compute a set of correction factors from the output measurements by computing crosstalk ratios based on spot brightness values for each of the calibration dye spots on each of the output channels wherein the spot brightness value includes the crosstalk contribution of all of the combinations of excitation wavelengths and dyes;

(c) apply the set of correction factors to quantitation data obtained from generated microarray images containing spots having three or more dyes with excitation or emission spectra to obtain crosstalk-corrected data; and (d) display or store in memory said crosstalk-corrected data.

10. The system as claimed in claim 9 wherein the imager is a microarray scanner which produces a dye image for each calibration dye spot by scanning the microarray substrate with a laser of proper wavelength for the particular dye.

11. The system as claimed in claim 9 wherein the substrate is a glass slide.

12. The system as claimed in claim 9 wherein each of the channels is optimized for a different dye.

13. The system as claimed in claim 10 wherein the microarray scanner is a confocal laser microarray scanner.

14. The system as claimed in claim 9 wherein each of the dyes is a fluorescent dye.

15. The system as claimed in claim 9 wherein the number of calibration dye spots is more than or equal to the number of dyes.

16. The system as claimed in claim 9 wherein the calibration dye spots are hybridized target DNA and fluorescently labeled probe DNA.

* * * * *